United States Patent
Santhanam et al.

(10) Patent No.: US 10,290,233 B2
(45) Date of Patent: May 14, 2019

(54) PHYSICAL DEFORMABLE LUNG PHANTOM WITH SUBJECT SPECIFIC ELASTICITY

(71) Applicants: THE REGENTS OF THE UNIVERSITY OF CALIFORNIA, Oakland, CA (US); UNIVERSITY OF CENTRAL FLORIDA RESEARCH FOUNDATION, INC., Orlando, FL (US)

(72) Inventors: Anand P. Santhanam, Culver City, CA (US); Olusegun Ilegbusi, Oviedo, FL (US)

(73) Assignees: THE REGENTS OF THE UNIVERSITY OF CALIFORNIA, Oakland, CA (US); UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 53 days.

(21) Appl. No.: 15/208,876

(22) Filed: Jul. 13, 2016

(65) Prior Publication Data
US 2017/0018205 A1 Jan. 19, 2017

Related U.S. Application Data

(63) Continuation of application No. PCT/US2015/011651, filed on Jan. 15, 2015.
(Continued)

(51) Int. Cl.
*A61B 6/00* (2006.01)
*G09B 23/30* (2006.01)
(Continued)

(52) U.S. Cl.
CPC .............. *G09B 23/30* (2013.01); *A61B 6/032* (2013.01); *A61B 6/466* (2013.01); *A61B 6/50* (2013.01);
(Continued)

(58) Field of Classification Search
CPC combination set(s) only.
See application file for complete search history.

(56) References Cited

U.S. PATENT DOCUMENTS 7,577,546 B2 * 8/2009 Subramaniam ......... G06T 17/20
702/167
7,577,547 B2 * 8/2009 Subramaniam ......... G06T 17/20
702/167
(Continued)

FOREIGN PATENT DOCUMENTS

JP 2011-524754 A 9/2011

OTHER PUBLICATIONS

Korean Intellectual Property Office (KIPO), International Search Report and Written Opinion dated Apr. 30, 2015, PCT international application No. PCT/US2015/011651, pp. 1-10, with claims searched, pp. 11-14. The relevance of non-English language reference JP 2011-524754 is set forth therein.
(Continued)

*Primary Examiner* — Tsung Yin Tsai
(74) *Attorney, Agent, or Firm* — O'Banion & Ritchey LLP; John P. O'Banion

(57) ABSTRACT

A system and method to integrate computational fluid dynamics (CFD) and radiotherapy data for accurate simulation of spatio-temporal flow and deformation in real human lung is presented. The method utilizes a mathematical formulation that fuses the CFD predictions of lung displacement with the corresponding radiotherapy data using the theory of Tikhonov regularization.

21 Claims, 4 Drawing Sheets

Related U.S. Application Data

(60) Provisional application No. 61/927,730, filed on Jan. 15, 2014.

(51) Int. Cl.
*G09B 23/28* (2006.01)
*A61B 6/03* (2006.01)
*A61B 34/10* (2016.01)
*A61N 5/10* (2006.01)
*G06T 7/246* (2017.01)
*G06F 19/00* (2018.01)
*G16H 50/50* (2018.01)

(52) U.S. Cl.
CPC ............ *A61B 6/5211* (2013.01); *A61B 6/583* (2013.01); *A61B 34/10* (2016.02); *A61N 5/1075* (2013.01); *G06F 19/00* (2013.01); *G06T 7/251* (2017.01); *G09B 23/28* (2013.01); *G09B 23/286* (2013.01); *G16H 50/50* (2018.01); *A61B 2034/105* (2016.02); *A61N 2005/1076* (2013.01); *G06T 2207/10076* (2013.01); *G06T 2207/10081* (2013.01); *G06T 2207/30061* (2013.01); *G06T 2207/30076* (2013.01)

(56) References Cited

U.S. PATENT DOCUMENTS

| | | | | |
|---|---|---|---|---|
| 2007/0231779 | A1* | 10/2007 | Santhanam | G09B 23/28 434/262 |
| 2009/0156933 | A1* | 6/2009 | Gerard | G06T 7/38 600/443 |
| 2009/0316972 | A1* | 12/2009 | Borenstein | A61B 6/583 382/131 |
| 2010/0041992 | A1* | 2/2010 | Ohuchi | A61B 8/08 600/443 |
| 2011/0093243 | A1 | 4/2011 | Tawhai | |
| 2011/0222081 | A1* | 9/2011 | Yi | G06T 17/00 358/1.9 |
| 2012/0041739 | A1* | 2/2012 | Taylor | A61B 5/02007 703/11 |
| 2012/0072193 | A1 | 3/2012 | De Backer | |
| 2012/0203530 | A1 | 8/2012 | Sharma et al. | |
| 2012/0232853 | A1* | 9/2012 | Voigt | G06F 19/321 703/1 |
| 2012/0237104 | A1* | 9/2012 | Fouras | A61B 5/08 382/132 |
| 2012/0283564 | A1 | 11/2012 | Ebbini et al. | |
| 2013/0085736 | A1* | 4/2013 | Reihsen | G16H 50/50 703/11 |
| 2013/0243294 | A1* | 9/2013 | Ralovich | G06T 7/0012 382/131 |
| 2014/0201126 | A1* | 7/2014 | Zadeh | G06K 9/627 706/52 |
| 2015/0049083 | A1* | 2/2015 | Bidne | G06T 19/006 345/420 |
| 2017/0116387 | A1* | 4/2017 | El-Zehiry | G16H 50/30 |
| 2017/0248708 | A1* | 8/2017 | Bordy | A61N 5/1071 |

OTHER PUBLICATIONS

European Patent Office (EPO), extended European search report (Communication) dated Nov. 16, 2016, related EPO application No. 15737617, pp. 1-10, with claims searched, pp. 11-13.

Seyfi, Behnaz et al., "Application of Fusion Algorithm to Human Lung Dynamics", Proceedings of the ASME International Mechanical Engineering Congress and Exposition 2012, vol. 2: Biomedical and Biotechnology, Nov. 5-9, 2012, p. 239-245.

Ilegbusi, Olusegun J. et al., "Modeling Airflow Using Subject-Specific 4DCT-Based Deformable Volumetric Lung Models", International Journal of Biomedical Imaging, vol. 2012, Jan. 1, 2012, pp. 1-10.

Rengier, F. et al., "3D printing based on imaging data: review of medical applications", International Journal of Computer Assisted Radiology and Surgery, vol. 5, No. 4, published online May 15, 2010, pp. 335-341.

Giesel, Frederik L. et al., "Rapid Prototyping Raw Models on the Basis of High Resolution Computed Tomographyy Lung Data for Respiratory Flow Dynamics", Academic Radiology, vol. 16, No. 4, Apr. 1, 2009, pp. 495-498.

* cited by examiner

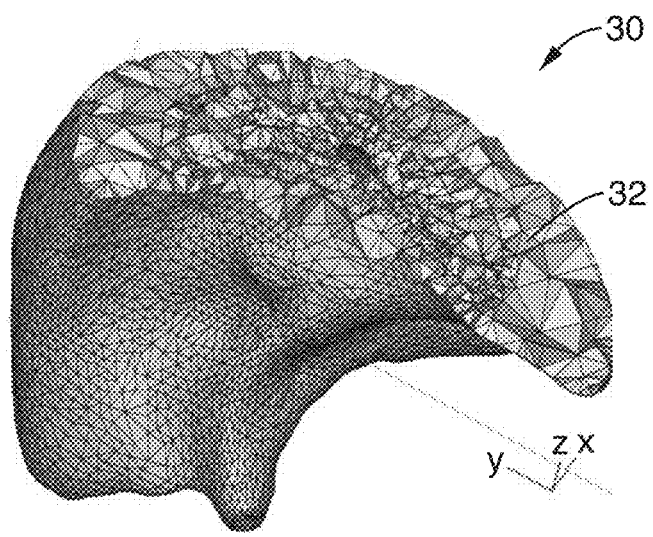
FIG. 2
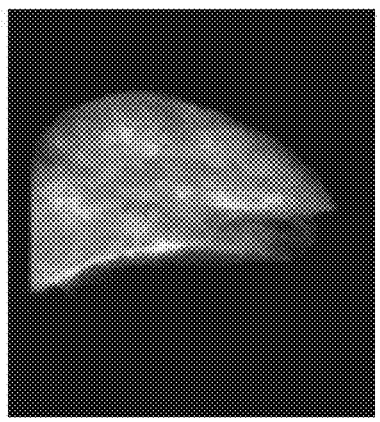 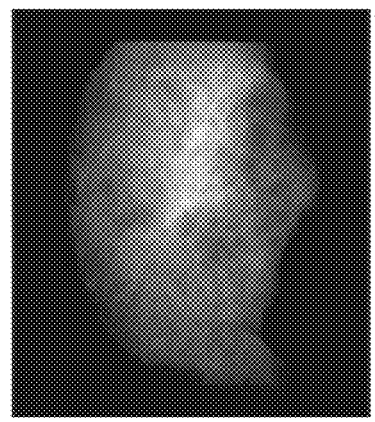
FIG. 3A          FIG. 3B
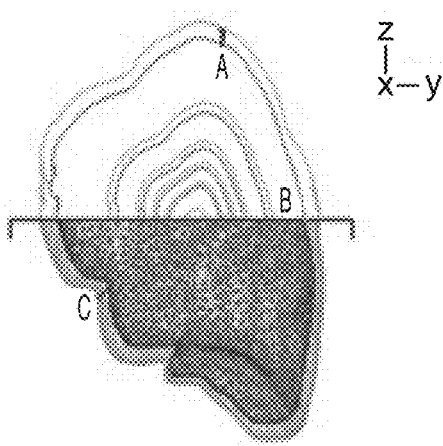
FIG. 4

PHYSICAL DEFORMABLE LUNG PHANTOM WITH SUBJECT SPECIFIC ELASTICITY

CROSS-REFERENCE TO RELATED APPLICATIONS

This application is a 35 U.S.C. § 111(a) continuation of PCT international application number PCT/US2015/011651 filed on Jan. 15, 2015, incorporated herein by reference in its entirety, which claims priority to, and the benefit of, U.S. provisional patent application Ser. No. 61/927,730 filed on Jan. 15, 2014, incorporated herein by reference in its entirety. Priority is claimed to each of the foregoing applications.

The above-referenced PCT international application was published as PCT International Publication No. WO 2015/109121 on Jul. 23, 2015, which publication is incorporated herein by reference in its entirety.

STATEMENT REGARDING FEDERALLY SPONSORED RESEARCHER DEVELOPMENT

This invention was made with Government support under 1200579, awarded by the National Science Foundation. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to estimation of tissue deformation, and more particularly to lung tissue deformation.

2. Background Discussion

In human lung dynamics, a good and precise estimation of lung deformation during breathing is critical for targeted radiation oncology. Specifically, knowledge of the lung and tumor deformation during respiration can improve the efficiency of the radiation therapy with reference to minimizing exposure to surrounding healthy tissue. For example, in radiation oncology, physical phantoms can be used as a treatment quality assurance (QA) tool for delivering a given radiotherapy treatment plan.

To date, there exists no physical lung phantom that both incorporates physically accurate material properties and attenuated X-ray beam sources X-ray attenuation similar to an actual lung anatomy.

Work has been done to determine the lung deformation during respiration. Some of these studies include the use of pure imaging methods, Inverse Deformation (ID) methods, and the coupling of imaging and inverse methods for estimation. However these experimental methods are purely image-based and so involve a lot of discrepancies. As a counterpart of measurement, numerical modeling to simulate flow and deformation in the lung of humans has been studied, ranging from fractal theory to macroscopic. Because of limitation of each method, it is difficult to obtain detailed information.

Accordingly, an object of the present description is physical phantom that incorporates both physically accurate material properties and tissue-equivalent radiological properties. Another object is a 4D imaging/treatment methodology incorporating a deformable phantom for performing QA analysis. Another object is a 3D bio-printing method to generate or "print" subject-specific phantoms that are not currently available. At least some of these objectives will be met in the description provided below.

BRIEF SUMMARY

Aspects of the present description are systems and methods for generating a deformable physical phantom of the human lung for radiotherapy applications.

Other aspects are systems and methods to develop polymer nanocomposite materials with unique elastic and radiological properties that mimic the human lung, and use the material for fabrication of 3D lung physical phantom. The desired material meets two specific criteria: (a) elastic property equivalency to human lung tissues; and (b) radiation-attenuation equivalency to the anatomy being represented (e.g. soft tissue, airways, capillaries etc.).

Such nanocomposites may consist of nanoparticles embedded in a polymer matrix. By varying the chemical and physical structure of the host matrix and nanoparticles, such as the size, orientation, distribution of coordination of the nanoparticles, and tailoring the matrix-particle interactions, the desired multi-functional properties, including expected excellent elastic and radiological response, can be realized.

Another aspect of the present description is a system and method for generating physical phantoms that can be used as a treatment quality assurance (QA) tool for delivering a given radiotherapy treatment plan, and in particular, could enable a quantitative assessment of the delivered dose distributions that will be necessary to reduce normal tissue irradiated volumes and consequently radiation side effects. Patient-specific organ phantoms as provided by the systems and methods of the present description allow for testing of different radiation delivery techniques, thereby fine-tuning the delivered radiation dose age prior to delivery to the actual patients.

Another aspect is a system and method to integrate computational fluid dynamics (CFD) and radiotherapy data for accurate simulation of spatio-temporal flow and deformation in real human lung. Specifically, the method of the present disclosure utilizes a mathematical formulation that fuses the CFD predictions of lung displacement with the corresponding radiotherapy data using the theory of Tikhonov regularization. The lung is assumed to behave as a poro-elastic medium with heterogeneous Young's modulus. The CFD scheme utilizes a flow-structure interaction (FSI) model to simultaneously solve the airflow equations and structural dynamics of the lung tissue, with allowance for interaction at the interface. The simulation is performed on a 3D lung geometry reconstructed from 4D CT scan dataset of real human patients. The predicted deformation is fused with inverse estimation data by means of the fusion algorithm to obtain the optimal results.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 2 is a computer generated output of a typical computational mesh generated and applied in the CFD model of latter step.

FIG. 3A and FIG. 3B are images of a 3D volumetric distribution of Young's modulus for the right lung at (FIG. 3A) lateral and (FIG. 3B) crania-caudal views.

FIG. 4 is an image of a computer-generated output of predicted lung deformation at t=1 sec for monitored nodes A, B, C in multi-layer CFD model.

DETAILED DESCRIPTION

Figure 1:
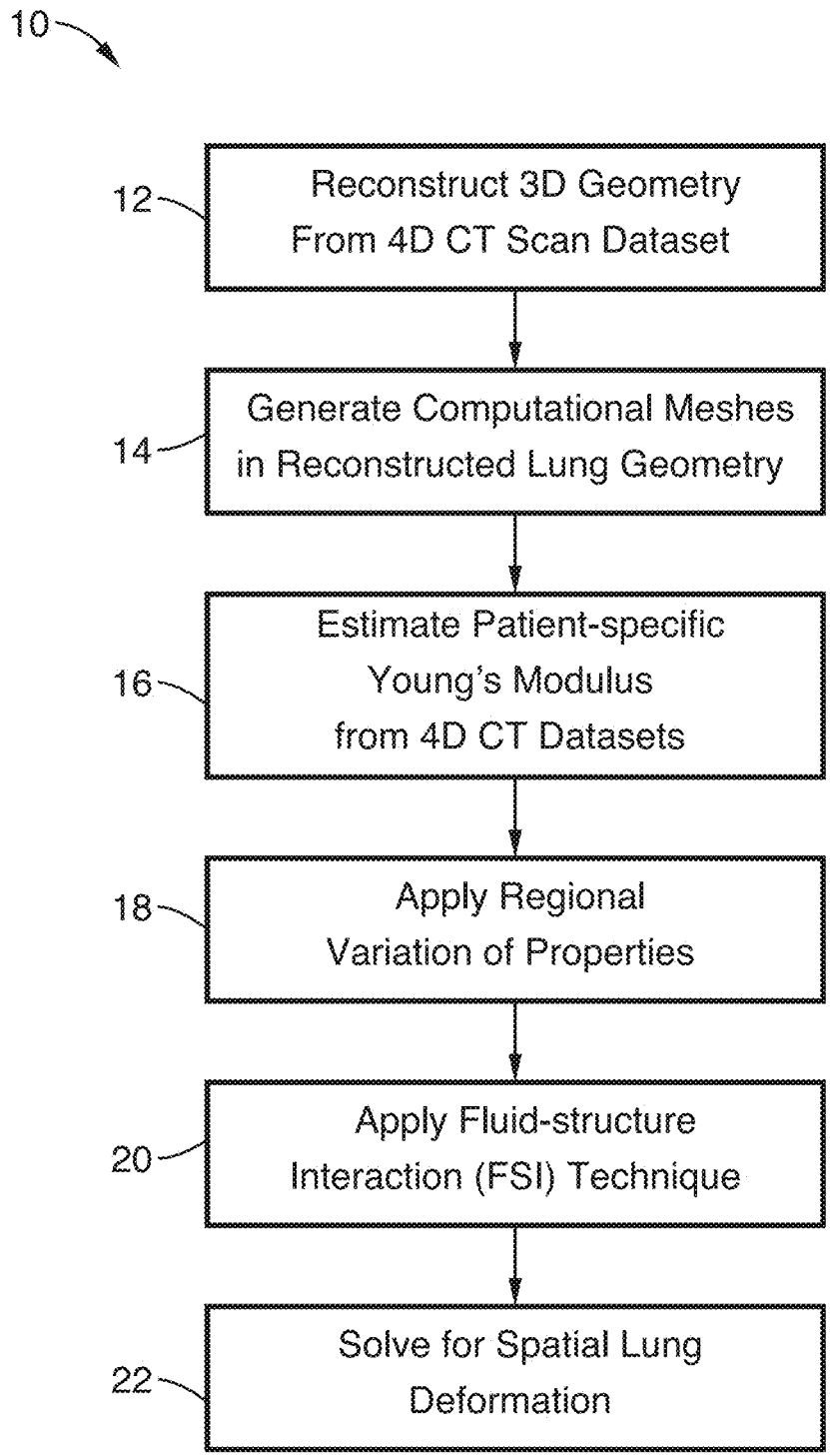
FIG. 1 shows a flow diagram detailing an exemplary CFD/imaging integration method in accordance with the present description.

The systems and methods of the present description incorporate a mathematical model, also referred to as a fusion algorithm that integrates the results of experimental data and computational fluid dynamics in order to obtain an optimal solution for accurate simulation of spatio-temporal flow and deformation in real human lung.

1. Fusion Algorithm

The fusion systems and methods of the present description comprise means of interpolating and extrapolating the scattered experimental (radiotherapy) data by the smooth curve obtained from the CFD solver. The existence of two datasets is assumed, one image-based experimental data, and the other computational. The fusion systems and methods of the present description incorporate a mathematical formulation that fuses the CFD predictions of lung displacement with the corresponding radiotherapy data using the theory of Tikhonov regularization.

a. Tikhonov Regularization Method

Used as a method of regularization of ill-posed problems (e.g. mathematical analysis of experimental data) Tikhonov regularization enables construction of an approximate solution which combines information from both experiment and a mathematical model.

The method applied in the present disclosure is based on the construction of regularizing operator $\Lambda(f_a, f_{CFD})$ by minimizing a smoothing or objective functional, $z^\alpha$, given by:

$$z^\alpha(\vec{x}) = \tfrac{1}{2}\alpha\rho(f_a(\vec{x}), f_{exp}(\vec{x})) + \tfrac{1}{2}\Lambda(f_a(\vec{x}), f_{CFD}(\vec{x})) \quad \text{Eq. 1}$$

In the above equation, $\alpha$ is the regularization parameter, $\rho(f_a, f_{exp})$ represents the discrepancy operator, $f_a$, $f_{exp}$ and $f_{CFD}$ represent approximate, experimental and CFD deformation vectors associated with a 3D anatomy respectively. Minimizing $z^\alpha$ is equivalent to minimizing the $\Lambda(f_a, f_{CFD})$ on the set of elements $f_a$ for which: $\rho(f_a, f_{exp}) = \sigma$, where $\sigma$ represents experimental data error.

The regularization method is accomplished in two steps: (i) finding the regularization operator and (ii) determining the regularization parameter.

The first step is accomplished by assuming that the space of functions is Hilbert space, which has a squared-integrable generalized derivative up to the $k^{th}$ order. The regularization operator is classified as either quantitative or qualitative; it is not unique and depends on the type of physical process and the data type. In the second step, $\alpha$ is determined from supplementary information pertaining to the problem, e.g., the noise level in $f_{exp}$. For purposes of the present disclosure, $\alpha$ is determined from the condition $\rho(f_a, f_{exp}) = \sigma$. One approach to determining the correct value for $\alpha$ is to define the discrepancy as standard square error.

Substituting the result from the two steps described above, the objective functional $z^\alpha(f_a, f_{exp}, f_{CFD})$ for a 3D domain is obtained as:

$$z^\alpha(\vec{x}) = \tfrac{1}{2}\alpha[f_{exp}(\vec{x}) - f_a(\vec{x})]^2 + \tfrac{1}{2}[f_a(\vec{x}) - f_{CFD}(\vec{x})]^2 + \tfrac{1}{2}\{\nabla\cdot[f_a(\vec{x}) - f_{CFD}(\vec{x})]\}^2 \quad \text{Eq. 2}$$

It is to be noted that in Eq. 2, $\alpha$ is solved iteratively and uses the solution of $f_a$ within each iteration.

b. Numerical Solution of the Objective Functional

Using results obtained from the CFD solver and experimental results obtained from a previous study of 4D-CT registration, a primary objective is to seek a numerical solution to minimize Eq. 2. For this purpose, finite element analysis is applied as follows. For each element, the minimum of objective functional can be obtained by differentiating with respect to nodal values in that specific element, so the functions in Eq. 2 are defined based on the nodal values. For each element, consider $k=1, 2 \ldots n$; where $n$ = number of nodes and $\vec{C}^e = (c_1, c_2 \ldots c_k)$ nodal value vector with nodal values components; $c_1, c_2 \ldots c_k$, then within each element approximate and CFD function are defined as:

$$f_a(\vec{x}) = \sum_{k=0}^{n} H(\vec{x}, \vec{x_k}) C(\vec{x_k}) \quad \text{Eq. 3}$$

$$f_{CFD}(\vec{x}) = \sum_{k=0}^{n} H(\vec{x}, \vec{x_k}) \Delta(\vec{x_k}) \quad \text{Eq. 4}$$

In the above equations, $H(x, x_k)$ is the interpolation function, in fact approximate and CFD functions are summed over all nodal values in the element, and $\Delta(x, x_k)$ is a nodal value vector. By defining the approximate and CFD functions in terms of nodal values, the next step is to plug in these functions in Eq. 2, and differentiate with respect to nodal values to find the minimum objective functional in each element then:

$$z^\alpha(\vec{x}) = \tfrac{1}{2}\alpha[f_{exp}(\vec{x}) - \Sigma_{k=0}^{n} H(\vec{x}, \vec{x_k}) C(\vec{x_k})]^2 + \tfrac{1}{2} \Sigma_{k=0}^{n} I^2(\vec{x}, \vec{x_k})[C(\vec{x_k}) - \Delta(\vec{x_k})]^2 + \tfrac{1}{2} \Sigma_{k=0}^{n} I^2(\vec{x}, \vec{x_k}) [C(\vec{x_k}) - \Delta(\vec{x_k})]^2 + \tfrac{1}{2} \Sigma_{k=0}^{n} J^2(\vec{x}, \vec{x_k}) [C(\vec{x_k}) - \Delta(\vec{x_k})]^2 + \tfrac{1}{2} \Sigma_{k=0}^{n} M^2(\vec{x}, \vec{x_k}) [C(\vec{x_k}) - \Delta(\vec{x_k})]^2 \quad \text{Eq. 5}$$

where I, J and M are new interpolation functions and are defined as:

$$I(\vec{x}, \vec{x_k}) = \frac{\partial H(\vec{x}, \vec{x_k})}{\partial x} \quad \text{Eq. 6}$$

$$J(\vec{x}, \vec{x}_k) = \frac{\partial H(\vec{x}, \vec{x}_k)}{\partial y} \qquad \text{Eq. 7}$$

$$M(\vec{x}, \vec{x}_k) = \frac{\partial H(\vec{x}, \vec{x}_k)}{\partial z} \qquad \text{Eq. 8}$$

Differentiating Eq. 8 with respect to $c_k$:

$$\begin{aligned}
z^\alpha(\vec{x}) = &\tfrac{1}{2}\alpha[f_{exp}(\vec{x}) - \Sigma_{k=0}^n H(\vec{x}, \vec{x}_k) \\
&C(\vec{x}_k)]^2 + \tfrac{1}{2}\Sigma_{k=0}^n H^2(\vec{x}, \vec{x}_k)[C(\vec{x}_k) - \\
&\Delta(\vec{x}_k)]^2 + \tfrac{1}{2}\Sigma_{k=0}^n I^2(\vec{x}, \vec{x}_k)[C(\vec{x}_k) - \\
&\Delta(\vec{x}_k)]^2 + \tfrac{1}{2}\Sigma_{k=0}^n J^2(\vec{x}, \vec{x}_k)[C(\vec{x}_k) - \\
&\Delta(\vec{x}_k)]^2 + \tfrac{1}{2}\Sigma_{k=0}^n M^2(\vec{x}, \vec{x}_k)[C(\vec{x}_k) - \Delta(\vec{x}_k)]^2
\end{aligned} \qquad \text{Eq. 9}$$

where:

$$L_k(\vec{x}, \vec{x}_k) = \frac{\partial \vec{H}^e(\vec{x}, \vec{x}_k)}{\partial c_k} \qquad \text{Eq. 10}$$

$$N_k(\vec{x}, \vec{x}_k) = \frac{\partial I_k(\vec{x}, \vec{x}_k)}{\partial c_k} \qquad \text{Eq. 11}$$

$$P_k(\vec{x}, \vec{x}_k) = \frac{\partial J_k(\vec{x}, \vec{x}_k)}{\partial c_k} \qquad \text{Eq. 12}$$

$$R_k(\vec{x}, \vec{x}_k) = \frac{\partial M_k(\vec{x}, \vec{x}_k)}{\partial c_k} \qquad \text{Eq. 13}$$

and where $\tau^e$ is an indicator of whether experimental data exists in the current element or not.

If no experimental data exists in the element, the value of $\tau^e$ becomes zero and the first integral in Eq. 8 eliminates, otherwise the value of $\tau^e$ changes to one. Minimizing the equation by setting the LHS of Eq. 9 to zero, we let:

$$D(\vec{x}, \vec{x}_k) = H(\vec{x}, \vec{x}_k)L_k(\vec{x}, \vec{x}_k) + I(\vec{x}, \vec{x}_k)N_k(\vec{x}, \vec{x}_k) + \\ J(\vec{x}, \vec{x}_k)P_k(\vec{x}, \vec{x}_k) + M(\vec{x}, \vec{x}_k)R_k(\vec{x}, \vec{x}_k) \qquad \text{Eq. 14}$$

$$0 = \tau^e \alpha \left[ f_{exp}(\vec{x}) + \sum_{k=0}^n H^e(\vec{x}, \vec{x}_k)C(\vec{x}_k)L_k(\vec{x}, \vec{x}_k) \right] + \\ \sum_{k=0}^n D(\vec{x}, \vec{x}_k)[C(\vec{x}_k) - \Delta(\vec{x}_k)] \qquad \text{Eq. 15}$$

Eq. 15 can be further simplified as:

$$0 = \tau^e \alpha \left[ f_{exp}(\vec{x}) + \sum_{k=0}^n HL^e(\vec{x}, \vec{x}_k)C^e(\vec{x}_k) \right] + \\ \sum_{k=0}^n D(\vec{x}, \vec{x}_k)[C(\vec{x}_k) - \Delta(\vec{x}_k)]. \qquad \text{Eq. 16}$$

Next, we let:

$$D'(\vec{x}, \vec{x}_k) = D(\vec{x}, \vec{x}_k) + \tau^e \alpha HL^e(\vec{x}, \vec{x}_k) \qquad \text{Eq. 17}$$

$$0 = \tau^e \alpha f_{exp}(\vec{x}) + \sum_{k=0}^n D'(\vec{x}, \vec{x}_k)C^e(\vec{x}_k) - \sum_{k=0}^n D(\vec{x}, \vec{x}_k)\Delta(\vec{x}_k) \qquad \text{Eq. 18}$$

$$\sum_{k=0}^n D'(\vec{x}, \vec{x}_k)C^e(\vec{x}_k) = \sum_{k=0}^n D(\vec{x}, \vec{x}_k)\Delta(\vec{x}_k) - \tau^e \alpha f_{exp}(\vec{x}) \qquad \text{Eq. 19}$$

Now, it can be seen that we have two convolutions on either side of the formulation, so we now apply HSH transformations on either side to get the following relation for $C^e(\vec{x}_k)$. As a first step towards this process, we rewrite the $C(\vec{x}_k)$ and $\Delta(\vec{x}_k)$ using Hyper Spherical coordinates with a rotational invariant. They are written as:

$$C(\vec{x}_k) = C(R_{(\theta_k, \varphi_k, \chi_k)}(\theta_0, \varphi_0, \chi_0)) \qquad \text{Eq. 20}$$

$$\Delta(\vec{x}_k) = \Delta(R_{(\theta_k, \varphi_k, \chi_k)}(\theta_0, \varphi_0, \chi_0)) \qquad \text{Eq. 21}$$

In the above two equations, $(\theta_k, \varphi_k, \chi_k)$ represent the coordinate system for $x_k$ and $(\theta_0, \varphi_0, \chi_0)$ represent the coordinate origin. We now expand the formulation in the above equation using HSH transformation:

$$C(R_{(\theta_k, \varphi_k, \chi_k)}(\theta_0, \varphi_0, \chi_0)) = \\ \Sigma_{\lambda_1} \Sigma_{l_1} \Sigma_{m_1} \Sigma_{n_1} C_{\lambda_1 l_1 m_1} Y_{\lambda_1 l_1 n_1} S_{\lambda_1 m_1 n_1}(\theta_k, \varphi_k, \chi_k) \qquad \text{Eq. 22}$$

$$\Delta(R_{(\theta_k, \varphi_k, \chi_k)}(\theta_0, \varphi_0, \chi_0)) = \\ \Sigma_{\lambda_1} \Sigma_{l_1} \Sigma_{m_1} \Sigma_{n_1} \Delta_{\lambda_1 l_1 m_1} Y_{\lambda_1 l_1 n_1} S_{\lambda_1 m_1 n_1}(\theta_k, \varphi_k, \chi_k) \qquad \text{Eq. 23}$$

In the above two equations, the term S refers to the 3D HSH transformation of the SO(3) rotation. We now expand D and D' using HSH transformation as follows:

$$D(\theta, \varphi, x, \theta_k, \varphi_k, x_k) = \\ \sum_{\lambda_2} \sum_{l_2} \sum_{\lambda'_2} \sum_{l'_2} \sum_{m'_2} D_{\lambda_2 l_2 \lambda'_2 l'_2 m'_2} (Y^*_{\lambda'_2 l_2 m'_2}, (\theta_k, \varphi_k, \chi_k) \\ Y_{\lambda'_2 l'_2 m'_2}(\theta, \varphi, \chi) \qquad \text{Eq. 24}$$

$$D'(\theta, \varphi, x, \theta_k, \varphi_k, x_k) = \\ \sum_{\lambda_2} \sum_{l_2} \sum_{\lambda'_2} \sum_{l'_2} \sum_{m'_2} D'_{\lambda_2 l_2 \lambda'_2 l'_2 m'_2} (Y^*_{\lambda_2 l_2 m'_2}(\theta_k, \varphi_k, \chi_k) \\ Y_{\lambda'_2 l'_2 m'_2}(\theta, \varphi, \chi) \qquad \text{Eq. 25}$$

The term $\tau^e \lambda f_{exp}(\vec{x})$, which is on the RHS of Eq. 19, can be expanded as:

$$\tau^e \alpha f_{exp}(\theta, \varphi, x) = \sum_\lambda \sum_l \sum_m \tau^e \alpha f_{exp}(\theta, \varphi, \chi) \delta(\lambda) \delta(l) \delta(m) \qquad \text{Eq. 26}$$

where $\delta$ is the Dirac delta function.

The first term of the RHS of Eq. 19 can be expanded as:

$$\sum_{\lambda_1} \sum_{l_1} \sum_{m_1} \sum_{n_1} \sum_{\lambda_2} \sum_{l_2} \sum_{\lambda'_2} \sum_{l'_2} \sum_{m'_2} \Delta_{\lambda_1 l_1 m_1} D_{\lambda_2 l_2 \lambda'_2 l'_2 m'_2} S_{\lambda_1 m_1 n_1}(\theta_k, \\ \varphi_k, \chi_k) Y_{\lambda'_2 l'_2 m'_2}(\theta_0, \varphi_0, \chi_0) X_{\lambda_1 l_1 n_1 \lambda'_2 l'_2 m'_2} \qquad \text{Eq. 27}$$

where:

$$X_{\lambda_1 l_1 n_1 \lambda_2 l'_1 m'_2} = \delta_{\lambda_1 \lambda_2} \delta_{l_1 l_2} \delta_{n_1 m_2'} \qquad \text{Eq. 28}$$

The term can be further simplified as:

$$\Sigma_{\lambda_1}\Sigma_{l_1}\Sigma_{m_1}\Sigma_{\lambda_2}\Sigma_{l_2}\Sigma_{m_2}\Delta_{\lambda_1 l_1 m_1}D_{\lambda_1 l_1 \lambda_2 l_2 n_1}S_{\lambda_1 m_1 n_1}(\theta_k,\varphi_k,\chi_k)$$
$$Y_{\lambda_2' l_2' n_1}(\theta_0,\varphi_0,\chi_0)+Q(\theta,\varphi,\chi) \qquad \text{Eq. 29}$$

where $Q(\theta, \varphi, \chi)$ is a constant.

Similarly, the LHS of equation (19) can be simplified using HSH transformation:

$$\sum_{\lambda_1}\sum_{l_1}\sum_{m_1}\sum_{\lambda_2}\sum_{l_2}\sum_{n_1} C_{\lambda_1 l_1 m_1} D'_{\lambda_1 l_1 \lambda_2 l_2 n_1} \qquad \text{Eq. 30}$$

$$S_{\lambda_1 m_1 n_1}(\theta_k, \varphi_k, \chi_k) Y_{\lambda_2' l_2' n_1}(\theta_0, \varphi_0, \chi_0)$$

Equating the frequency coefficients, we get:

$$C_{\lambda_1 l_1 m_1} = \frac{\sum_{\lambda_2}\sum_{l_2}\sum_{n_1} D'_{\lambda_1 l_1 \lambda_2 l_2 n_1} * \Delta_{\lambda_1 l_1 m_1}}{\sum_{\lambda_2}\sum_{l_2}\sum_{n_1} D_{\lambda_1 l_1 \lambda_2 l_2 n_1}} \qquad \text{Eq. 31}$$

for $\lambda_1 l_1 m_1 \neq 0$, and $$C_{000} = \frac{\sum_{\lambda_2}\sum_{l_2}\sum_{n_1} D'_{00\lambda_2 l_2 n_1} * \Delta_{000} + [\text{constant } Q(\theta, \varphi, \chi)]}{\sum_{\lambda_2}\sum_{l_2}\sum_{n_1} D_{00\lambda_2 l_2 n_1}} \qquad \text{Eq. 32}$$

It can be seen that the formulation is analytical in nature, i.e. for known values of $f_{exp}$ and the subsequent nodal values of the CFD analysis, $C_{\lambda_1 l_1 m_1}$ can be calculated and ultimately the $f_a$ can be estimated. The formulation by itself is a direct solution.

c. CFD Model

The human lung considered is assumed to be a heterogeneous poro-elastic medium with anisotropic properties employed. The flow-structure interaction (FSI) technique is applied to simultaneously predict the air flow and deformation in the lung. The governing equations for both fluid flow and structural dynamics were solved using ADINA commercial CFD code.

The Young's modulus data and geometry are obtained from 4D CT scans of real human patients, thus integrating CFD with imaging.

FIG. 1 shows a flow diagram detailing the various steps involved in an exemplary CFD/imaging integration method 10 in accordance with the present description. The first step 12 is to reconstruct 3D geometry of real human lung from a 4D CT scan dataset. In a preferred embodiment, multimodal imaging is coupled with elastography techniques provide the geometry and elastic property data for step 12. The benefit of multi-modal imaging stems from the fact that the strain exhibited by lung tissues vary based on the stimulus observed during the imaging. Such stimulus includes airflow during 4DCT imaging, cardiac-induced lung motion during cardiac-gated MRI, etc. For every stimulus, a large number of lung voxels may remain undisturbed. However, a combination of multi-modal image analysis ensures that all the lung voxels display a non-zero strain for at least one of the imaging modalities.

Next, at step 14, computational meshes 32 are generated in the reconstructed lung geometry 30. FIG. 2 is a computer generated output of a typical computational mesh 32 generated and applied in the CFD model of latter step 22. It should be noted that FIG. 2 shows a cutout of a section of reconstructed lung lobe 30 for clarity.

Referring back to FIG. 1, at step 16 the patient-specific Young's Modulus from 4DCT datasets is estimated. Data from prior studies and experiments may be used in estimating Young's Modulus. A more concise description of the estimation step 16 is further described with respect to the estimation of volumetric deformation operator, or "experimental method" detailed below. The estimated elasticity will be utilized for CFD modeling of the lung biomechanics in step 22.

At step 18, the method allows for regional variation of properties, if any are present.

At step 20, the Fluid-Structure Interaction (FSI) technique is applied as described in further detail below.

At step 22, the method 10 solves for spatial lung deformation, e.g. using an ADINA CFD solver, or the like. There are 34654 nodes in the right lung in the mesh 32 shown in FIG. 2 used in the onion CFD model 3. The skewed nature of some meshes 32 via FIG. 2 appears to indicate that the number of volume meshes used in the analysis may benefit from further revision. However it should be emphasized that the bulk of the lung comprises relatively slow-flowing (diffusing) fluid and additional grid refinement is not necessary for this significant portion of the lung. With regards to the structural analysis, the fact that the elastic property is being measured and used directly may reduce the impact of the limited meshes.

Application of the fluid-structure interaction (FSI) step 20 involves solution of the coupled poro-elastic flow-structure interaction (FSI) equation with non-homogeneous and anisotropic tissue properties. This coupled field approach involves the solution of the Richard's Equation for the local lung pressure and velocity distributions, given by:

$$\frac{\partial p}{\partial t} = \nabla \cdot \left[\frac{k}{\mu_f}(\nabla p + \rho g)\right] - \frac{\partial}{\partial t}\left(\frac{\partial u}{\partial x} + \frac{\partial v}{\partial y} + \frac{\partial w}{\partial z}\right) \qquad \text{Eq. 33}$$

where $\phi$ and k represent the porosity and permeability of the tissue respectively, $\beta$, and $\mu$ represent the compressibility and viscosity of air respectively, p is the local pressure (pore pressure), and u, v, w are the three components of the deflection (deformation) vector for the tissue.

Equation 33 is coupled to the lung elastic deformation by the presence of the dilatation (final term) in the equation. This term is supplied by solving for the elastic deformation field, u, from the following poro-elastic version of the Navier's equation:

$$G\nabla^2 \vec{u} + \frac{G}{1-2v}\nabla(\nabla \cdot \vec{u}) = \nabla p - \vec{F} \qquad \text{Eq. 34}$$

where G and v are the tissue Shear Modulus and Poisson ratio, respectively, and $\vec{F}$ is an external body force term that can include thermal effects as desired.

Note that in Eq. 34, G represents anisotropic shear modulus. The method 10 assumes a simplified model of orthogonal anisotropy in global xy, yz and xz planes at this stage. However, since the geometry is not symmetric, this assumption may be relaxed to allow the anisotropic properties to follow local curvature in order to exhibit correct deformation. These equations are solved in step 22 for individual, specific patient lung geometries (e.g. using ADINA computational code in a preferred embodiment) in order to generate spatial distribution of the lung deformation for the CFD model.

d. Estimation of Volumetric Deformation Operator (Experimental Method)

Referring to estimation step 16, the deformation operator of 3D volumetric human lung is estimated via values of airflow and volumetric displacement as input to estimate the deformation operator in terms of Green's function (GF).

The Cartesian coordinates (X, Y, Z) of voxel positions of the 3D lung model is taken as input and an HS coordinate $(1,\theta,\varphi,\chi)$ is assigned to each voxel. The voxel positions are parameterized using a ray projection method in a way that the centroid of the lung voxels has the zero vectors as the hyper-spherical coordinate values.

For both the surface and volumetric lung deformation, a heterogeneous Green's Function (GF) based formulation is considered. The structural and functional constants estimated for the surface lung dynamics are specifically used for the volumetric lung dynamics. The GF for the volumetric lung is reformulated in the spectral domain using Hyper-Spherical Harmonic (HSH) transformation, which are the 3D extension of Spherical Harmonic (SH). Upon simplification, the HSH coefficients of the displacement are represented as a product of the HSH coefficients of the applied force and the deformation operator as shown in Eq. 35:

$$d_{\lambda_1 l_1 m_1 \lambda_2 l_2 m_2} = \left(\frac{8\pi^2}{2\lambda_1+1}\right) f_{\lambda_1 l_1 m_1} \rho_{\lambda_2 l_2 m_2} \quad \text{Eq. 35}$$

where $\rho_{\lambda_2 l_2 m_2}$ and $f_{\lambda_1 l_1 m_1}$ represent the value of displacement and applied force respectively, which are represented by their HSH coefficients.

From Eq. 3, the deformation operator can be estimated in terms of their spherical harmonic coefficients. The term $$\frac{8\pi^2}{2\lambda_1+1}$$

in the above equation refers to the normalization factor of the SO(3) rotation group.

2. CFD/Experimental Results

The following presents preliminary results obtained from the experimental and CFD models, which may themselves function as input into the CFD/imaging integration method 10.

The estimated deformation operator is associated with the voxel point, which was considered as the center in Eq. 3). The HSH parameterization is performed for each voxel. Once parameterized, the deformation operator for each voxel is then estimated. For every lung voxel, the operation is repeated with the voxel considered as the origin.

FIG. 3A and FIG. 3B show the initial results of the normalized inverse of the Young's modulus, which represents the regions with local expansion for the right lung of a human subject using 4DCT and repeat 4DCT imaging, at lateral and crania-caudal view respectively.

FIG. 4 shows an image of predicted lung deformation at one respiration stage (t=1 sec) for monitored nodes A, B, C in a multi-layer CFD model. Three nodes marked A, B, C in FIG. 4 were monitored, and their displacements along the x, y and z coordinate directions are predicted and analyzed over several breathing cycles. The upper part of the figure is a cut-off view to illustrate the evolution of selected layers from the initial state over the specified duration. The figure exhibits both directional deformation as well as expansion.

Figure 5A:
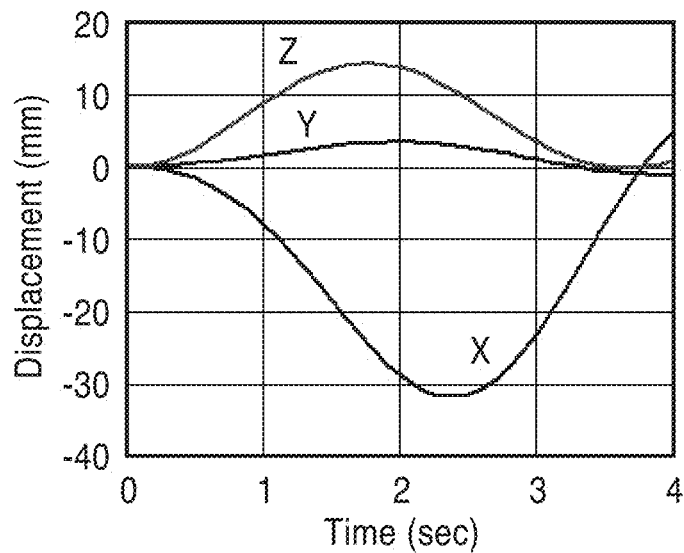
FIG. 5A, FIG. 5B and FIG. 5C show predicted displacement for nodes A, B, C of FIG. 4, respectively.
Figure 5B:
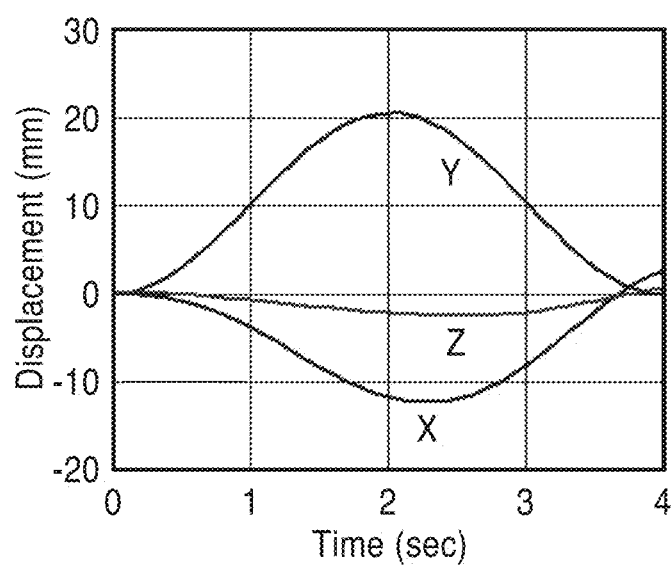
Figure 5C:
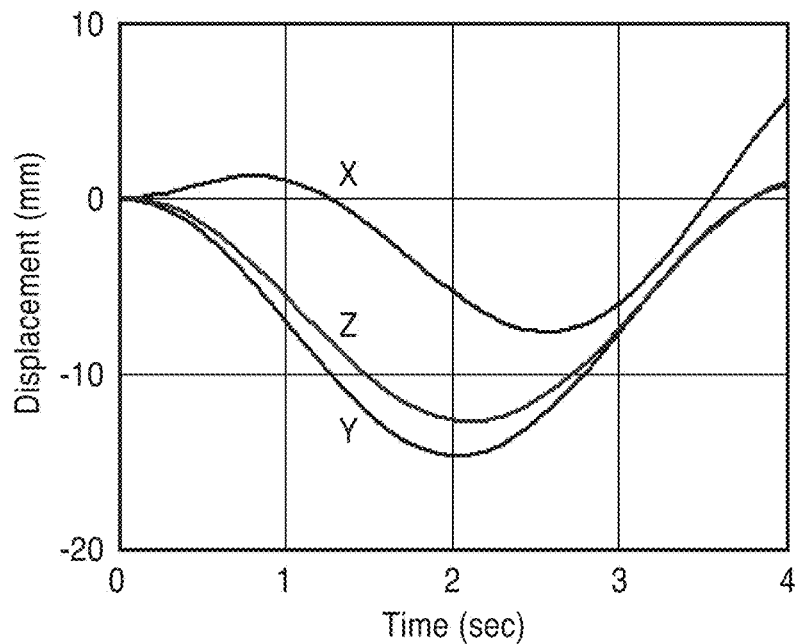
Figure 6:
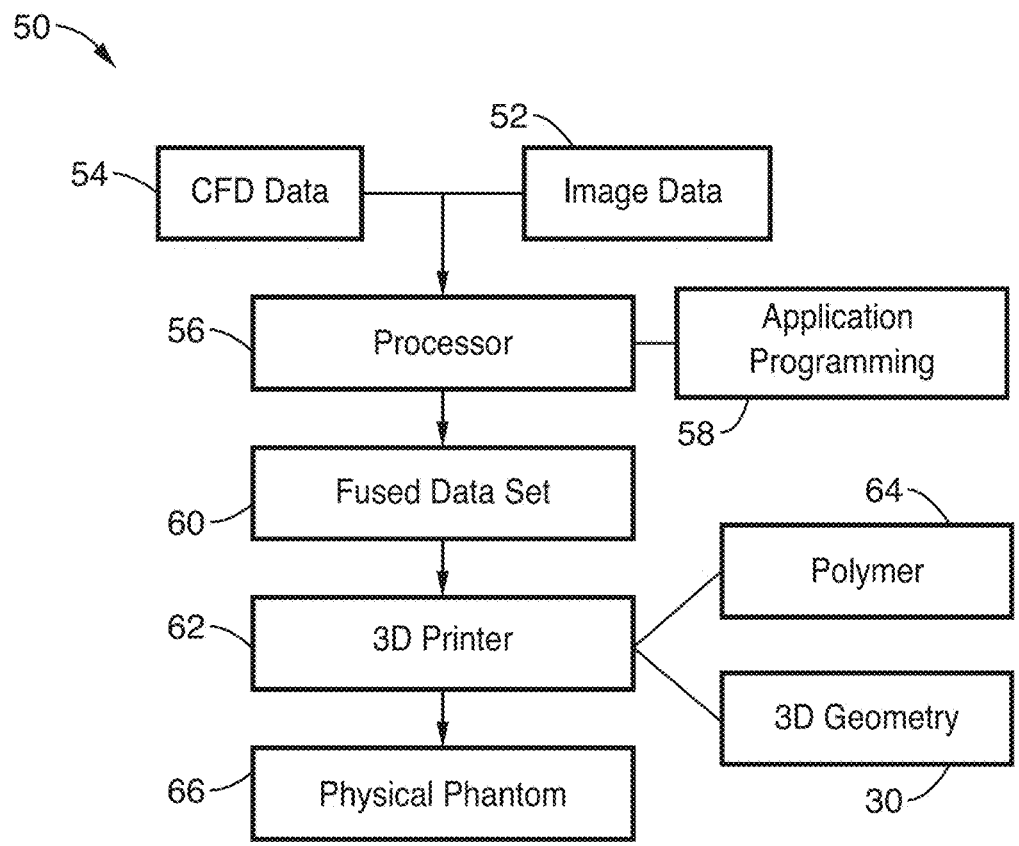
FIG. 6 shows a schematic system view of a phantom generator in accordance with the present description.

FIG. 5A, FIG. 5B, and FIG. 5C shows the x,y,z displacements of monitored nodes A, B and C, respectively, over one respiration cycle. The displacement trajectories are distorted from the sinusoidal pressure condition. The peak x displacement for node A is located at t=2.4 s, which lags the peak inlet pressure at t=2.0 s by 0.4 s. The peak z displacement for node A is 0.2 s ahead of the peak inlet pressure. A similar hysteresis phenomenon is observed for nodes B and C.

3. Applications

Referring to the schematic system view of phantom generator 50, the biomechanical modeling results (e.g. CFD data 54) are integrated with the multi-modal imaging data 52 by means of the fusion algorithm or CFD/imaging integration method 10 in the form of application programming 58 operable on computer processor 56 to generate fused data set 60 comprising unique elastic properties of the real human lung. These elastic properties, in turn, constitute one of the two primary constraints to the synthesis of polymer nanocomposite material. The synthesized material 64 may be integrated with the 3D geometry 30 reproduced from the radiological data for additive manufacturing via a 3D printer 62 of a physical lung phantom 66.

Such lung phantom 66 will uniquely have the capability to physically simulate airflow and cardiac induced deformation. The elastic properties that the physical phantom 66 would use will enable the model to undergo the same deformations as the subject for a given airflow and cardiac pulsation. The systems and methods of the present disclosure may be used to estimate elastic properties of lung that can be used for actual experiments pertaining to lung airflow, volume, and cardiac pulsation. Estimating a physical lung phantom 66 in accordance with the methods and systems of the present disclosure would incorporate multiple stress sources (breathing, cardiac etc.) so that there is no lung region with zero strain.

The systems and methods disclosed above may be used to generate a polymer nanocomposite material 64 that has the combined elastic and radiological properties from fused data set 60 for a physical lung phantom material 66. In addition, such nanocomposite materials would be compatible with additive manufacturing processes for fabrication of a high quality lung phantom simulated lung with an accurate 3D geometry and expected performance for clinical applications.

The generated lung phantom data 60 from the systems and methods of the present disclosure may be 3D printable (e.g. via 3D printer 62) for rapid prototyping purposes, for generating a physical lung phantom 66 on a subject-specific basis. Specifically, lung cancer patients undergoing radiotherapy may greatly benefit from the availability of such a patient-specific lung phantom 66 can be used for performing quality assurance QA analyses before their treatment is initiated. Developing Strategies for adaptive manufacturing of a physical lung phantom may make rapid prototyping of deformable patient anatomy a reality.

The lung phantom data 60 and/or physical lung phantom 66 of the present disclosure may also be used to improve Quality Assurance (QA) methods, such as the following four categories:

(i) Treatment QA: The lung phantom data 60 and/or physical lung phantom 66 may be used for verification of the dose delivery on a deformable anatomy. The phantom 66 can be placed in an external beam radiotherapy setup and the treatment can be delivered as planned and quantified.

(ii) Imaging QA: The lung phantom data 60 and/or physical lung phantom 66 may be configured for evaluating performance of multiple 3D and 4D imaging studies of deformable anatomy as a way of addressing multi-modal image acquisition artifacts. Specifically, this phantom will enable lung treatments to be translated from a CT based environment to MR based environment, leading to a better sparing of normal organs.

(iii) Gating QA: The lung phantom data 60 and/or physical lung phantom 66 may be configured to quantify the accuracy of gating methods (e.g. strain-gauge belt) during both imaging and treatment delivery.

(iv) Dose QA: The lung phantom data 60 and/or physical lung phantom 66 may be configured to enable Monte-Carlo dose calculation of photon/proton sources to be experimentally verified.

In conclusion, an algorithm was developed for fusing the experimental and CFD data. A multi-layer poro-elastic model of lung was employed to provide the CFD solution for the lung deformation. It was shown that CFD solutions can be combined with the inverse dynamics data using theory of Tikhonov regularization. Further accuracy of CFD solution may be enhanced through fusion with the experimental data beyond the classical comparison between the two sets of data. In addition, the smooth curve of CFD model helps to filter the noise in experimental data. While the examples disclosed herein are particularly described with respect to lung tissue deformation and it is appreciated that the fusion method of the present disclosure may be applied to other tissues or any branch of engineering to reduce computational cost and to analyze the experimental measurements provided that a-priori physical models and experimental data provide.

Embodiments of the present technology, and in particular, the methods disclosed in FIG. 1 through FIG. 4, may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A system for simulation of spatio-temporal flow and deformation in human tissue, comprising: a processor; and programming executable on the processor for: acquiring radiotherapy imaging data of the tissue; acquiring computational fluid dynamics (CFD) data corresponding to predictions of tissue displacement; and fusing the imaging data with the CFD data to obtain a fused dataset of the tissue.

2. The system of any preceding embodiment, wherein the tissue comprises a human lung.

3. The system of any preceding embodiment, wherein the imaging data comprises inverse estimation data of a CT scan dataset.

4. The system of any preceding embodiment, wherein the fused dataset is acquired using Tikhonov regularization.

5. The system of any preceding embodiment, wherein acquiring computational fluid dynamics (CFD) data comprises generating a flow-structure interaction model to simultaneously solve the airflow and structural characteristics of lung tissue.

6. The system of any preceding embodiment, wherein fusing the inverse estimation data with the CFD data comprises: reconstructing 3D geometry of the lung from the CT scan dataset; generating one or more computational meshes in the reconstructed 3D geometry of the lung; estimating patient-specific Young's Modulus data from the CT scan datasets; applying fluid-structure interaction (FSI) calculations to calculate one or more of air flow and deformation characteristics of the lung; and calculating spatial lung deformation as a function of the FSI calculations and reconstructed lung geometry.

7. The system of any preceding embodiment, wherein the imaging data comprises multi-modal imaging data.

8. The system of any preceding embodiment, wherein the fused data set comprises one or more unique elastic properties of the imaged human lung.

9. The system of any preceding embodiment, further comprising: a 3D printer; said printer configured for generating a polymeric lung phantom comprising one or more elastic properties of the imaged human lung.

10. A method for simulation of spatio-temporal flow and deformation in human tissue, comprising: acquiring radiotherapy imaging data of the tissue; acquiring computational fluid dynamics (CFD) data corresponding to predictions of tissue displacement; and fusing the imaging data with the CFD data to obtain a fused dataset of the tissue.

11. The method of any preceding embodiment, wherein the tissue comprises a human lung.

12. The method of any preceding embodiment, wherein the imaging data comprises inverse estimation data of a CT scan dataset.

13. The method of any preceding embodiment, wherein the fused dataset is acquired using Tikhonov regularization.

14. The method of any preceding embodiment, wherein acquiring computational fluid dynamics (CFD) data comprises generating a flow-structure interaction model to simultaneously solve the airflow and structural characteristics of lung tissue.

15. The method of any preceding embodiment, wherein fusing the inverse estimation data with the CFD data comprises: reconstructing 3D geometry of the lung from the CT scan dataset; generating one or more computational meshes in the reconstructed 3D geometry of the lung; estimating patient-specific Young's Modulus data from the CT scan datasets; applying fluid-structure interaction (FSI) calculations to calculate one or more of air flow and deformation characteristics of the lung; and calculating spatial lung deformation as a function of the FSI calculations and reconstructed lung geometry.

16. A method provided in any of the previous embodiments, wherein the imaging data comprises multi-modal imaging data.

17. The method of any preceding embodiment, wherein the fused data set comprises one or more unique elastic properties of the imaged human lung.

18. The method of any preceding embodiment, further comprising: generating a polymeric lung phantom as a function of the fused data set, the polymeric lung phantom comprising one or more elastic properties of the imaged human lung.

19. The method of any preceding embodiment, wherein the polymeric lung phantom comprises one or more polymer nanocomposite materials having one or more unique elastic and radiological properties that mimic the imaged lung.

20. A method for generating a lung phantom simulating spatio-temporal flow and deformation in a target lung tissue, comprising: acquiring radiotherapy imaging data of the target lung tissue; acquiring computational fluid dynamics (CFD) data corresponding to predictions of tissue displacement; fusing the imaging data with the CFD data to obtain a fused dataset of the target lung tissue; and generating a polymeric lung phantom as a function of the fused data set, the polymeric lung phantom comprising one or more elastic properties of the target lung tissue.

21. The method of any preceding embodiment, wherein the polymeric lung phantom comprises one or more polymer nanocomposite materials having one or more unique elastic and radiological properties that mimic the imaged lung.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system for simulation of spatio-temporal flow and deformation in human tissue, comprising:
   a processor; and
   programming executable on the processor for:
      acquiring radiotherapy imaging data of the tissue;
      acquiring computational fluid dynamics (CFD) data corresponding to predictions of tissue displacement;
      fusing the imaging data with the CFD data to obtain a fused dataset of the tissue;
      wherein the fused data set comprises one or more unique radiological or elastic properties of the tissue; and
   a patient-specific, physical organ phantom comprising the one or more unique radiological or elastic properties of the imaged tissue from the fused data set;
   said organ phantom physically simulating a unique induced deformation of the imaged tissue; and
   said organ phantom having a radiation-attenuation equivalency to the imaged tissue.

2. A system as recited in claim 1, wherein the tissue comprises a human lung and the patient-specific organ phantom comprises a lung phantom.

3. A system as recited in claim 2, wherein the imaging data comprises inverse estimation data of a CT scan dataset.

4. A system as recited in claim 3, wherein the fused dataset is acquired using Tikhonov regularization.

5. A system as recited in claim 3, wherein acquiring computational fluid dynamics (CFD) data comprises generating a flow-structure interaction model to simultaneously solve the airflow and structural characteristics of lung tissue.

6. A system as recited in claim 3, wherein fusing the inverse estimation data with the CFD data comprises:
   reconstructing 3D geometry of the lung from the CT scan dataset;
   generating one or more computational meshes in the reconstructed 3D geometry of the lung;
   estimating patient-specific Young's Modulus data from the CT scan datasets;

applying fluid-structure interaction (FSI) calculations to calculate one or more of air flow and deformation characteristics of the lung; and calculating spatial lung deformation as a function of the FSI calculations and reconstructed lung geometry.

7. A system as recited in claim 2:

said lung phantom physically simulating the unique lung airflow and cardiac induced deformation of the imaged human lung; and said lung phantom having a radiation-attenuation equivalency to the imaged human lung.

8. A system as recited in claim 7, further comprising:

a 3D printer;

said printer configured for generating a polymeric lung phantom.

9. A system as recited in claim 7, wherein the lung phantom comprises one or more polymer nanocomposite materials having one or more unique elastic and radiological properties that mimic the imaged lung.

10. A method as recited in claim 9, wherein the imaging data comprises multi-modal imaging data.

11. A system as recited in claim 1, wherein the imaging data comprises multi-modal imaging data.

12. A method for simulation of spatio-temporal flow and deformation in human tissue, comprising:

acquiring radiotherapy imaging data of the tissue;

acquiring computational fluid dynamics (CFD) data corresponding to predictions of tissue displacement;

fusing the imaging data with the CFD data to obtain a fused dataset of the tissue;

wherein the fused data set comprises one or more unique radiological or elastic properties of the imaged human tissue; and generating a patient-specific, physical organ phantom comprising the one or more unique radiological or elastic properties of the imaged tissue from the fused dataset said organ phantom physically simulating a unique induced deformation of the imaged tissue; and said organ phantom having a radiation-attenuation equivalency to the imaged tissue.

13. A method as recited in claim 12, wherein the tissue comprises a human lung and the organ phantom comprises a lung phantom;

wherein the imaging data comprises inverse estimation data of a CT scan dataset.

14. A method as recited in claim 13:

said lung phantom physically simulating the unique lung airflow and cardiac induced deformation of the imaged human lung; and said lung phantom having a radiation-attenuation equivalency to the imaged human lung.

15. A method as recited in claim 14, wherein generating a patient-specific organ phantom comprises generating a polymeric lung phantom by 3D printing one or more polymer nanocomposite materials to have the one or more unique elastic and radiological properties that mimic the imaged lung.

16. A method as recited in claim 13, wherein acquiring computational fluid dynamics (CFD) data comprises generating a flow-structure interaction model to simultaneously solve the airflow and structural characteristics of the imaged lung tissue.

17. A method as recited in claim 13, wherein fusing the inverse estimation data with the CFD data comprises:

reconstructing 3D geometry of the lung from the CT scan dataset;

generating one or more computational meshes in the reconstructed 3D geometry of the lung;

estimating patient-specific Young's Modulus data from the CT scan datasets;

applying fluid-structure interaction (FSI) calculations to calculate one or more of air flow and deformation characteristics of the lung; and calculating spatial lung deformation as a function of the FSI calculations and reconstructed lung geometry.

18. A method for generating a lung phantom simulating spatio-temporal flow and deformation in a target lung tissue, comprising:

acquiring radiotherapy imaging data of the target lung tissue;

acquiring computational fluid dynamics (CFD) data corresponding to predictions of tissue displacement;

fusing the imaging data with the CFD data to obtain a fused dataset of the target lung tissue;

wherein the fused data set comprises one or more unique radiological or elastic properties of the imaged lung tissue;

generating a patient-specific polymeric lung phantom as a function of the fused data set, the polymeric lung phantom comprising the one or more unique radiological and elastic properties of the target lung tissue;

said lung phantom physically simulating a unique induced deformation of the target lung tissue; and said lung phantom having a radiation-attenuation equivalency to the target lung tissue.

19. A method as recited in claim 18, wherein the polymeric lung phantom comprises one or more polymer nanocomposite materials having the one or more unique elastic and radiological properties that mimic the imaged lung.

20. A system for simulation of spatio-temporal flow and deformation in human tissue, comprising:

a processor; and programming executable on the processor for:

acquiring radiotherapy imaging data of the tissue;

acquiring computational fluid dynamics (CFD) data corresponding to predictions of tissue displacement;

fusing the imaging data with the CFD data to obtain a fused dataset of the tissue;

wherein the fused data set comprises one or more unique radiological or elastic properties of the tissue; and a patient-specific organ phantom comprising the one or more unique radiological or elastic properties of the imaged tissue from the fused data set;

wherein the tissue comprises a human lung and the patient-specific organ phantom comprises a lung phantom;

said lung phantom physically simulating the unique lung airflow and cardiac induced deformation of the imaged human lung; and said lung phantom having a radiation-attenuation equivalency to the imaged human lung.

21. A method for simulation of spatio-temporal flow and deformation in human tissue, comprising:

acquiring radiotherapy imaging data of the tissue;

acquiring computational fluid dynamics (CFD) data corresponding to predictions of tissue displacement;

fusing the imaging data with the CFD data to obtain a fused dataset of the tissue;

wherein the fused data set comprises one or more unique radiological or elastic properties of the imaged human tissue; and generating a patient-specific organ phantom comprising the one or more unique radiological or elastic properties of the imaged tissue from the fused dataset;

wherein the tissue comprises a human lung and the organ phantom comprises a lung phantom;

wherein the imaging data comprises inverse estimation data of a CT scan dataset;

said lung phantom physically simulating the unique lung airflow and cardiac induced deformation of the imaged human lung; and said lung phantom having a radiation-attenuation equivalency to the imaged human lung.

* * * * *